United States Patent [19]

Kubicek

[11] 4,188,327
[45] Feb. 12, 1980

[54] SULFOLENE HYDROGENATION

[75] Inventor: Donald H. Kubicek, Bartlesville, Okla.

[73] Assignee: Phillips Petroleum Company, Bartlesville, Okla.

[21] Appl. No.: 940,674

[22] Filed: Sep. 8, 1978

[51] Int. Cl.$^2$ .......................................... C07D 333/48
[52] U.S. Cl. ...................................................... 549/87
[58] Field of Search ...................................... 260/332.1

[56] References Cited

U.S. PATENT DOCUMENTS 3,544,430  12/1970  Mihm ................................ 260/332.1

*Primary Examiner*—A. Siegel

[57] ABSTRACT

A process for converting sulfolene compounds to sulfolane compounds comprising contacting at least one sulfolene compound with hydrogen in the presence of a metal hydrogenation catalyst and an effective amount of an $SO_2$ neutralizer or scavenger comprising an alkali metal or alkaline earth metal hypohalite salt and optionally a tertiary amine. In one embodiment the sulfolene feed is pretreated with alkali metal or alkaline earth metal hypohalite salt prior to being subjected to hydrogenation to neutralize residual sulfur compounds in the feed thereby minimizing catalyst poisoning.

14 Claims, No Drawings

SULFOLENE HYDROGENATION

This invention relates to an improved process for the catalytic hydrogenation of sulfolene. In accordance of another aspect, this invention relates to a process for the hydrogenation of sulfolene compounds wherein hydrogenation is effected in the presence of at least one of alkali metal and alkaline earth metal hypohalite salts. In accordance with another aspect, this invention provides a method for neutralizing excess sulfur dioxide and other sulfur compounds present in sulfolene feeds for hydrogenation of sulfolene to sulfolane by the addition of at least one of an alkali and alkaline earth metal hypohalite salts. In accordance with a further aspect, this invention relates to a process for the hydrogenation of sulfolene in the presence of an alkali metal or alkaline earth metal hypohalite salt and optionally a tertiary amine.

Sulfolane compounds are saturated five-membered rings of four carbon atoms and a sulfur atom, the latter having two oxygen atoms directly attached thereto. The structural formula of the simplest unsubstituted sulfolane is

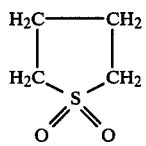

The most widely used sulfolane compound is the material known as sulfolane, i.e., 2,3,4,5-tetrahydrothiophene-1,1-dioxide which is especially valuable as a selective solvent. Another especially widely used sulfolane compound is 2,4-dimethylsufolane which also has been used as a selective solvent to separate aromatic hydrocarbons from petroleum fractions. Other uses for sulfolanes are in pesticidal compositions and intermediates in the production of various organic chemicals.

Sulfolanes are generally prepared by reacting sulfur dioxide with a conjugated diene to form a sulfolene. The resulting sulfolene is then catalytically hydrogenated to form the sulfolane. Sulfur dioxide is always present after the formation of the sulfolene and it must be removed before the hydrogenation step since it acts as a catalyst poison. Several methods have been proposed to remove the excess sulfur dioxide before hydrogenation. These methods are generally described in U.S. Pat. Nos. 3,622,598; 3,544,430; 3,514,469; 3,417,103; 3,152,144; 3,077,479 and 2,451,298. The most noteworthy methods involve the use of hydrogen peroxide which converts the sulfur dioxide to sulfur trioxide which in turn results in the formation of a dilute sulfuric acid solution that can be later neutralized. All of these methods exhibit various disadvantages. For example, increased process time results when a neutralization step is employed. Also, more hydrogenation catalyst is used than generally required even though hydrogen peroxide is added to neutralize the sulfur dioxide. Apparently, traces of sulfur dioxide remain to poison some of the catalyst charged.

Accordingly, an object of this invention is to provide an improved process as for the hydrogenation of sulfolenes.

Another object of this invention is to provide $SO_2$ neutralizer or scavenger material effective for improving hydrogenation of sulfolenes to sulfolanes.

A further object of this invention is to provide materials that effectively neutralize residual sulfur containing compounds and sulfolene feeds so as to increase conversion during hydrogenation and at the same time require less catalyst.

Further aspects as well as the several advantages of this invention will become apparent to those skilled in the art from the following discussion and appended claims. In accordance with the invention, a process is provided which comprises contacting at least one sulfolene compound with hydrogen in the presence of a metal hydrogenation catalyst and an effective amount of at least one of an alkali metal and an alkaline earth metal hypohalite salt as sulfur dioxide neutralizers or scavengers under hydrogenation conditions sufficient to effectively convert sulfolene compounds to sulfolane compounds.

In accordance with one embodiment of the invention, the sulfolene feed containing sulfur containing catalyst poisons is pretreated with at least one of an alkali metal and an alkaline earth metal hypohalite salt to neutralize detrimental sulfur compounds present in the feed before hydrogenation and thereby prevent catalyst poisoning.

In accordance with another embodiment of the invention, hydrogenation of sulfolene to sulfolane is carried out in the presence of an alkali metal or alkaline earth metal hypohalite salt and optionally a tertiary amine.

SULFOLENE-SULFOLANE

The term "sulfolene compound" as employed herein defines generically the unsubstituted and substituted unsaturated compounds comprising or containing a sulfolene nucleus, i.e., a five-membered ring of four carbon atoms and a sulfur atom with a single olefinic linkage between two adjacent carbon atoms of said ring, and two oxygen atoms each of which is directly attached to said sulfur atom. Thus, the generic term "a sulfolene compound" covers the unsubstituted and substituted sulfolenes, viz., the 3-sulfolenes having the general structure

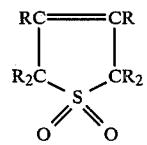

and the 2-sulfolenes having the structure wherein each R is individually

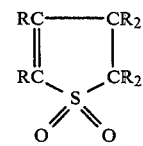

selected from the group consisting of hydrogen, hydrocarbon radicals, heterocyclic radicals, and inorganic radicals and combinations thereof which do not interfere with the hydrogenation reaction. Those compounds wherein each R is individually selected from the group consisting of hydrogen and hydrocarbon radicals having from one to eight carbon atoms are presently preferred. Suitable hydrocarbon radicals include alkyl, aryl, cycloalkyl, a combinations thereof. The following representative sulfolene compounds are suggested to those skilled in the art as being operable in this invention: 3-sulfolene, 2-sulfolene, 3-methyl-2-sulfolene, 2-methyl-3-sulfolene, 3-methyl-3-sulfolene, 2,4-dimethyl-3-sulfolene, 3-ethyl-3-sulfolene, and their homologues, as well as other sulfolene compounds, and mixtures thereof.

Similarly, the term "sulfolane compound" as used herein refers to a hydrogenated sulfolene compound, which can be either substituted or unsubstituted. The structural formula of the sulfolane compounds therefore is

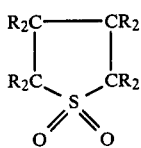

wherein R is as defined hereinabove, with at least one R on each of two previously unsaturated adjacent carbon atoms being hydrogen.

ALKALI OR ALKALINE EARTH METAL HYPOHALITE SALTS

The alkali or alkaline earth metal hypohalite salts useful in this invention are employed as sulfur dioxide neutralizers or scavengers and are represented by the formulas

| $M(OX)_n$ | or | $M'(OX)X$ |
|---|---|---|
| (I) | | (II) | wherein M in formula (I) is a metal from Group IA or IIA of the periodic table such as Li, Na, K, Rb, Cs, Be, Mg, Ca, Sr, or Ba; M' is formula (II) is a metal from Group IIA of the periodic table; X is a halogen such as F, Cl, Br, I but preferably Cl or Br; and n is 1 or 2 depending on the valence of the metal cation employed. Examples of such salts are NaOCl (sodium hypochlorite), KOCl (potassium hypochlorite), Ca(OCl)$_2$ (calcium hypochlorite), Ba(OCl)$_2$ (barium hypochlorite), Ca(OCl)Cl, and the like, and mixtures thereof.

A significant excess of hypohalite salt employed in this invention should be avoided since it can also interfere with hydrogenation catalysts. It is generally preferred in the present invention to limit the use of metal hypohalite salts to less than about $5.5 \times 10^{-3}$ moles per mole of sulfolene compound being hydrogenated. The exact amount of metal hypohalite salt employed will vary depending on the amount of excess sulfur dioxide present and on whether a vacuum removal step for the sulfur dioxide is used. The metal hypohalite is added to the reaction mixture prior to the addition of the hydrogenation catalyst.

TERTIARY AMINES

The tertiary amines which can be optionally employed in this invention are generally defined in U.S. patent 3,928,385 which is incorporated herein by reference. Specific examples include trimethylamine, triisobutylamine, N-methyldiethylamine, tridodecylamine, N-methyl-N-ethylpropylamine, N,N-dimethylbutylamine, N-ethyldipropylamine, triphenylamine, tribenzylamine, tri-p-tolylamine, tricyclohexylamine, N,N,N',N'-tetramethylethylenediamine, triethylenediamine, etc., and mixtures thereof.

Hexamethylenetetramine, the presently preferred tertiary amine, is a colorless, odorless and crystalline compound with the formula $(CH_2)_6N_4$. Hexamethylenetetramine is also known as: 1,3,5,7-tetra-azatricyclo [3.3.1.1$^{3.7}$]decane; methenamine; hexamethyleneamine; hexamine; formin; aminoform and urotropin.

The tertiary amine will generally be employed in an amount in the range of from about 0.001 to about 2 weight percent based on the sulfolene compound to be hydrogenated. The amine can be dissolved in a solvent if desired and can be admixed with the sulfolene feed prior to contacting the feed with the catalyst.

HYDROGENATION CATALYSTS

Hydrogenation catalysts which can be used in this invention include any of those known in the art useful in the catalytic hydrogenation of sulfolenes to sulfolanes. A preferred class of hydrogenation catalysts are those which comprise the metal hydrogenation catalysts, such as those containing or consisting of nickel, cobalt, copper, platinum, palladium or mixtures of these metals as well as mixtures of these metals with other metals such as iron, zinc, chromium, cadmium, etc. These metals can be used in finely divided form such as, for example, Raney nickel or can be suitably supported on a support such as kieselguhr, aluminum oxide, diatomaceous earth and the like. The catalyst can be charged portionwise or all at once. Generally, 1 to 5 wt. % catalyst based on the amount of sulfolene present is employed.

SOLVENT

The catalytic hydrogenation is preferably carried out with the sulfolene compound in the liquid state, for example, by maintaining it above its melting point (but below its thermal decomposition temperature) or in solution in a suitable solvent such as water, benzene, dioxane, alcohols, such as methyl, ethyl, isopropyl or tertiary butyl alcohol, the sulfolane compound itself and the like. The amount of solvent used can vary and generally will be in the range of about 5 to about 60 weight percent, preferably about 15 to about 40 weight percent of total solvent-sulfolene mixture. The use of a solvent permits better control over the temperature of the rapid and exothermic hydrogenation reaction.

REACTION CONDITIONS

The reaction temperatures and pressures can vary over wide ranges. In fact, any temperature is operable at which the reaction mixture is liquid and which is below that at which the materials decompose. Preferred operation conditions are about 25° C. (77° F.) to about 66° C. (150° F.) and at a hydrogen pressure in the range from about 0.689 MPa (100 psig) to about 2.068 MPa (300 psig) or higher and requiring from about one to about six hours for the hydrogenation to be completed.

Following completion of the hydrogenation reaction, the sulfolane product can be recovered by conventional procedures. Generally, this comprises first cooling the reaction mixture to remove the catalyst and any salts (i.e. metal halide by-products) and fractionating the filtered reaction mixture to remove solvent and unreacted sulfolene compound.

The following examples are presented in further illustration of the present invention.

EXAMPLE I

This example and runs described therein employ hydrogen peroxide as a sulfur dioxide neutralizer or scavenger and is considered the control for the present invention.

To a 300 milliliter stainless steel autoclave equipped with a mechanical stirrer, cooling coils, thermocouple and baffles was charged 59.0 grams (0.50 moles) of freshly prepared sulfolene (from butadiene and sulfur dioxide) that contained some excess sulfur dioxide and 50.0 grams of distilled water. The contents were mildly heated to about 49° C. (120° F.) with stirring while a vacuum (100 mm Hg) was applied to physically remove as much excess sulfur dioxide as possible. After about 1.5 hrs. at 49° C. (120° F.), 0.6 grams of 30 weight percent hydrogen peroxide was added to the mixture and stirred for another 15–30 mins under vacuum. (If an amine is also to be added it is added at this point). One milliliter of Raney nickel (0.82 grams nickel) was added to the reactor, stirred for 5–10 mins. and then the reactor was pressured to 2.068 MPa (300 psig) with hydrogen and maintained at that pressure throughout the remainder of the run. The exothermic nature of the reaction caused the temperature to rise to about 57° C. (135° F.). When the temperature exceeded 150° F., the reaction mixture was cooled by means of the internal cooling coils. After about 2 hrs. the contents were cooled to ambient room temperature, hydrogen pressure released and the system flushed with nitrogen. The contents were removed, filtered, and the filtrate analyzed by gas-liquid chromatography (GLC) using a 6 ft. column packed with Carbowax 20 M and programmed at 30° C./min. between 50° C. and 250° C.; helium flow, 60 cc/min. The results of this run and others using hydrogen peroxide with and without an amine present are shown in Table I. These data show that without sulfur dioxide present, hydrogen peroxide can have a slight deleterious result (Runs 1 and 2) but can be overcome by the addition of more catalyst, Runs 6–8, and an amine. Increasing the amount of peroxide (Runs 3–5) has no large effect on conversion.

Effect of Hydrogen Peroxide as an $SO_2$ Neutralizer on the Percent Conversion of Sulfolene to Sulfolane

| Run No. | Raney Nickel, gms | $H_2O_2$, Moles × 10 | Amine[b] Moles × $10^{-3}$ | % Conversion of Sulfolene to Sulfolane |
|---|---|---|---|---|
| 1[a]. | 1.0 | 0 | — | 98.6 |
| 2[a]. | 1.0 | 1.76 | — | 89.4 |
| 3. | 1.0 | 1.76 | — | 43.2 |
| 4. | 1.0 | 3.52 | — | 38.0 |
| 5. | 1.0 | 5.28 | — | 57.7 |
| 6. | 1.0 | 3.52 | 0.71 | 18.5 |
| 7. | 1.5 | 3.52 | 0.71 | 76.1 |
| 8. | 2.0 | 3.52 | 0.71 | 92.4 |

[a].Recrystallized sulfolene. Contains no excess $SO_2$.
[b].Hexamethylene tetramine added as a 10 weight percent aqueous solution.

EXAMPLE II

This example describes the inventive runs wherein the $SO_2$-containing freshly prepared sulfolene was hydrogenated as in Example I except NaOCl was used instead of hydrogen peroxide with and without the presence of an amine. The results listed in Table II show improved percent conversion with an alkali metal hypohalite such as sodium hypochlorite, NaOCl supplied as a 5.25 wt % solution (Chlorox ®). However, excess NaOCl significantly decreases percent conversion (Runs 4 and 5). Likewise, increased quantities of amine also decrease percent conversion (Runs 7 and 8).

Table II

Effect of Sodium Hypochlorite as an $SO_2$ Neutralizer on the Percent Conversion of Sulfolene to Sulfolane

| Run No. | Raney Nickel, gms | NaOCl, Moles × $10^{-3}$ | Amine[a] Moles × $10^{-3}$ | % Conversion Sulfolene to Sulfolane |
|---|---|---|---|---|
| 1. | 1.0 | 1.76 | — | 63.6 |
| 2. | 1.0 | 3.52 | — | 94.6 |
| 3. | 1.0 | 5.29 | — | 99.6 |
| 4. | 1.0 | 7.05 | — | 95.2 |
| 5. | 1.0 | 10.56 | — | 38.3 |
| 6. | 1.0 | 5.29 | 0.71 | 99.3 |
| 7. | 1.0 | 5.29 | 1.07 | 66.4 |
| 8. | 1.0 | 5.29 | 1.43 | 50.7 |

[a]Hexamethylenetetramine added as a 10 weight percent aqueous solution.

EXAMPLE III

This example describes the inventive runs with and without the presence of an amine. The results listed in Table III show improved percent conversion with an alkaline earth metal hypohalite such as calcium hypochlorite, $Ca(OCl)_2$ supplied as a 25 weight percent aqueous solution.

Table III

Effect of Calcium Hypochlorite as an $SO_2$ Neutralizer on the Percent Conversion of Sulfolene to Sulfolane

| Run No. | Raney Nickel, gms | $Ca(OCl)_2$, Moles × $10^{-3}$ | Amine[a] Moles × $10^{-3}$ | % Conversion Sulfolene to Sulfolane |
|---|---|---|---|---|
| 1. | 1.0 | 2.78 | — | 77.3 |
| 2. | 1.0 | 4.18 | — | 99.2 |
| 3. | 0.50 | 2.78 | 0.71 | 78.8 |
| 4. | 0.75 | 2.78 | 0.71 | 90.0 |
| 5. | 1.00 | 2.78 | 0.71 | 98.7 |
| 6. | 1.50 | 2.78 | 0.71 | 99.0 |
| 7. | 2.0 | 2.78 | 0.71 | 99.5 |

[a]Hexamethylenetetramine supplied as a 10 weight percent aqueous solution.

SUMMARY

Tables IV and V summarize the data herein described and show that when a solution of sulfolene is pretreated with an alkali or alkaline earth metal hypochlorite before hydrogenation, a higher weight percent conversion to sulfolane is obtained than when the solution is pretreated with hydrogen peroxide. Likewise it is shown that at near equal concentrations, less Raney nickel is required for high weight percent conversion when alkali or alkaline earth metal hypohalite are employed as sulfur dioxide neutralizers then when hydrogen peroxide is employed for the same purpose.

Table IV

| Moles × $10^{-3}$ Neutralizer or Scavenger Employed | Weight % Conversion of Sulfolene to Sulfolane Using Various $SO_2$ Neutralizers (Scavengers) | | |
|---|---|---|---|
| | $H_2O_2$ | NaOCl | $Ca(OCl)_2$ |
| 1.76 | 43.2 | 63.6 | — |
| 3.52 | 38.0 | 94.6 | 77.3[a] |
| 5.29 | 57.5 | 99.2 | 99.2[b] |
| 7.05 | — | 95.2 | |
| 10.56 | — | 38.3 | |

[a]2.78 × $10^{-3}$ moles employed.
[b]4.18 × $10^{-3}$ moles employed.

Table V

| Raney Nickel, gms | Weight % Conversion of Sulfolene to Sulfolane Using Various SO$_2$ Neutralizers (Scavengers)[a] | | |
|---|---|---|---|
| | H$_2$O$_2$[b] | NaOCl[c] | Ca(OCl)$_2$[d] |
| 1.0 | 18.5 | 99.3 | 98.7 |
| 1.5 | 76.1 | — | 99.0 |
| 2.0 | 92.4 | — | 99.5 |

[a] Contains 0.71 moles × 10$^{-3}$ of hexamethylenetetramine.
[b] At 3.52 × 10$^{-3}$ moles concentration
[c] At 5.29 × 10$^{-3}$ moles concentration
[d] At 2.78 × 10$^{-3}$ moles concentration

I claim:

1. A process for converting sulfolene to sulfolane which comprises contacting
    (a) a feed of at least one sulfolene compound containing sulfur dioxide and other sulfur-containing catalyst poisons with
    (b) hydrogen in the presence of
    (c) a metal hydrogenation catalyst, and
    (d) an effective amount of sulfur dioxide neutralizers or scavengers comprising at least one of alkali metal and alkaline earth metal hypohalite salts under hydrogenation conditions including a temperature at which the reaction mixture is liquid and which is below that at which the materials decompose and sufficient to effectively convert said sulfolene compound to a sulfolane compound.

2. A process according to claim 1 wherein said feed is pretreated prior to hydrogenation by contacting with at least one of alkali metal and alkaline earth metal hypohalite salts in order to effect a higher weight percent conversion to a sulfolane compound.

3. A process according to claim 1 wherein said contacting is carried out additionally in the presence of (e) a tertiary amine compound.

4. A process according to claim 1 wherein (d) can be represented by the formulas

| M(OX)$_n$ | or | M'(OX)X |
|---|---|---|
| (I) | | (II) | wherein M is a metal selected from Group IA and IIA metal, M' is a metal selected from Group IIA metals, X is a halogen, and n is 1 or 2.

5. A process according to claim 1 wherein the amount of (d) present is less then about 5.5×10$^{-3}$ moles per mole of sulfolene compound being hydrogenated.

6. A process according to claim 1 wherein said hydrogenation conditions include liquid phase conditions and a temperature in the range of about 25 to about 66° C. and a hydrogen pressure of from about 0.689 MPa to about 2.068 MPa.

7. A process according to claim 1 for the conversion of sulfolene to sulfolane wherein (c) is Raney nickel catalyst and (d) is sodium hypochlorite or calcium hypochlorite.

8. A process according to claim 3 wherein (e) is hexamethylenetetramine.

9. A process according to claim 1 for the hydrogenation of sulfolene to said feed wherein sulfolene is pretreated by contacting with sodium hypochlorite and then contacted with hydrogen and a hydrogenation catalyst.

10. A process according to claim 1 wherein said feed (a) is a reaction product obtained on reacting a conjugated alkadiene and SO$_2$ and the reaction product contains sulfur-containing poisons detrimental to catalytic hydrogenation catalysts.

11. In a process for producing a sulfolane compound wherein a feed comprising a sulfolene compound containing sulfur dioxide and other sulfur-containing catalyst poisons is catalytically hydrogenated in the presence of a hydrogenation catalyst, the improvement comprising carrying out said hydrogenation step after first adding an effective amount of at least one of an alkali metal and alkaline earth metal hypohalite salt as sulfur dioxide neutralizers or scavengers to said feed.

12. A process according to claim 11 wherein said salt is sodium hypochlorite or calcium hypochlorite.

13. A process according to claim 11 wherein said hydrogenation is carried out in the presence of a tertiary amine.

14. A process according to claim 11 wherein the amount of said salt added to said feed is less than about 5.5×10$^{-3}$ moles per mole of sulfolene compound being hydrogenated which amount is sufficient to effectively neutralize residual sulfur dioxide and other low valent sulfur compounds and prevent catalyst poisoning of said hydrogenation catalyst.

* * * * *